(12) United States Patent
Fu et al.

(10) Patent No.: US 8,019,141 B2
(45) Date of Patent: Sep. 13, 2011

(54) SCAN CONVERSION METHOD AND DEVICE FOR COLOR ULTRASONIC IMAGING

(75) Inventors: Zhengpeng Fu, Shenzhen (CN); Yong Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 927 days.

(21) Appl. No.: 11/967,884

(22) Filed: Dec. 31, 2007

(65) Prior Publication Data

US 2009/0087056 A1    Apr. 2, 2009

(30) Foreign Application Priority Data

Sep. 27, 2007 (CN) .......................... 2007 1 0162366

(51) Int. Cl.
*A61B 8/00* (2006.01)

(52) U.S. Cl. ....................................... 382/131

(58) Field of Classification Search .......... 382/128–132, 382/916; 600/437, 443, 449, 453, 441, 455, 600/456
See application file for complete search history.

(56) References Cited

U.S. PATENT DOCUMENTS

| | | | |
|---|---|---|---|
| 5,390,674 A | 2/1995 | Robinson et al. | |
| 5,429,137 A | 7/1995 | Phelps et al. | |
| 6,370,264 B1 * | 4/2002 | Leavitt | 382/128 |
| 6,423,006 B1 * | 7/2002 | Banjanin | 600/453 |
| 7,722,540 B2 * | 5/2010 | Abe et al. | 600/443 |
| 7,744,538 B2 * | 6/2010 | Sumanaweera et al. | 600/455 |
| 2006/0184029 A1 * | 8/2006 | Haim et al. | 600/443 |

FOREIGN PATENT DOCUMENTS

| | | |
|---|---|---|
| CN | 1868407 A | 11/2006 |
| CN | 1891159 A | 1/2007 |
| JP | 2001000435 | 9/2001 |

* cited by examiner

*Primary Examiner* — Irakli Kiknadze
(74) *Attorney, Agent, or Firm* — Kory D. Christensen; Stoel Rives LLP (57) ABSTRACT

A scan conversion method and device for color ultrasonic imaging that uses conditional interpolation of neighboring points is disclosed.

18 Claims, 4 Drawing Sheets

SCAN CONVERSION METHOD AND DEVICE FOR COLOR ULTRASONIC IMAGING

RELATED APPLICATIONS

This application claims priority to Chinese Patent Application No. 200710162366.9, filed Sep. 27, 2007, which is hereby incorporated by reference in its entirety.

TECHNICAL FIELD

The present disclosure relates to scan conversion methods and devices for color ultrasonic imaging.

SUMMARY

Scan conversion based on an algorithm with conditional interpolation between neighboring points is disclosed.

DETAILED DESCRIPTION OF PREFERRED EMBODIMENTS

An ultrasonic diagnostic apparatus utilizes ultrasonic wave transmission in a human body to obtain ultrasonic characteristic information on structures of tissues and organs of the human body to form displays in various imaging modes. During examination of a patient, the information is displayed on a cathode ray tube (CRT) screen or a liquid crystal display (LCD) screen in real time.

Brightness mode (B-mode) is often used in imaging the geometrical shapes of tissue structures in the human body. The brightness of a dot displayed in a dot matrix on the CRT or LCD screen represents the amplitude of the ultrasonic echo. In B-mode, images of motion by some tissues (e.g., movement of the heart wall) can be directly detected. However, limitations on resolution in the ultrasonic technique mean that smaller structures cannot be detected in B-mode. Such limitations can be apparent in some applications. For example, in cardiac imaging, echo features of some important structures (e.g., the inside of the blood vessel) may be very weak.

Colored blood flow imaging (C-mode) is an improved imaging method based on B-mode, in which the result of ultrasonic imaging includes information on the motion of the blood flow in the blood vessel, and separate Doppler scanning is used in addition to the scanning similar to that in B-mode. Along the Doppler-scan line, information on the velocity of the movement of the object and on variance and energy of velocity can be estimated and coded with colors to form colored images that are simultaneously displayed with gray-scale images in B-mode. The images finally displayed include gray-scale images and colored images, in which the gray-scale images indicate geometrical structures of various tissues of the human body and the colored images indicate the features of motion by the blood in the tissues.

Figure 1:
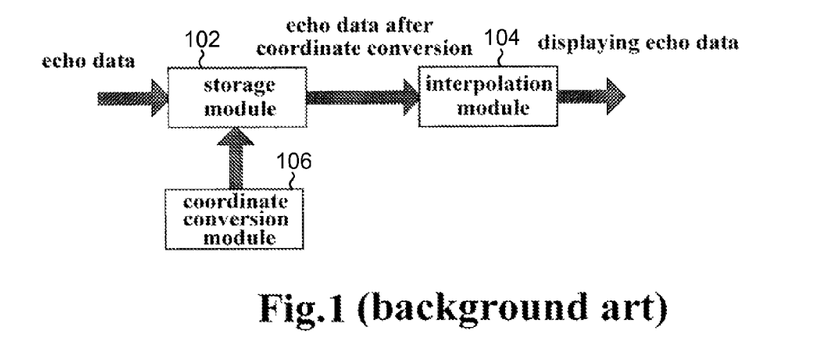
FIG. 1 is a schematic block diagram of a digital scan converter.

The real-time imaging techniques in both B-mode and C-mode require a conversion, termed a "scan conversion," for converting the information contained in the ultrasonic echo signals to a display on a CRT or LCD screen. Conventionally, scan conversion employs a digital scan converter (DSC). As shown in FIG. 1, a DSC may include a storage module 102, a coordinate conversion module 104, and an interpolation module 106. The storage module 102 is a memory for storing ultrasonic echo data. The coordinate conversion module 106 is for converting the coordinates on the CRT or LCD screen into those corresponding to the information contained in the ultrasonic echo signals.

Figure 2:
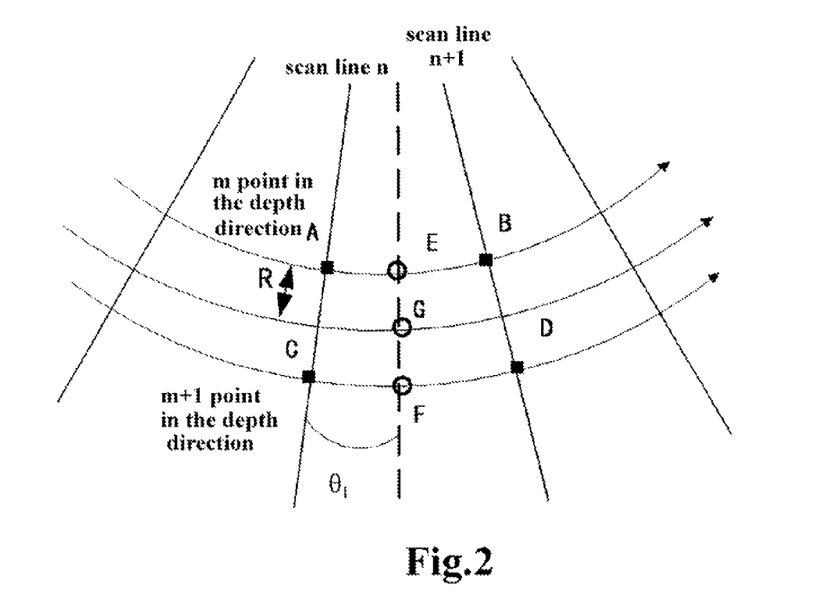
FIG. 2 is a graph depicting an algorithm for interpolating between neighboring points.

Generally, the ultrasonic information gathered from the section examined is specified in polar coordinates, and yet the display pixels in the standard television raster display system are specified in Cartesian coordinates. Thus conversion between the polar coordinates and the Cartesian coordinates is necessary. Usually, only a few pixel points on the Cartesian coordinates can correspond one-to-one to points on the polar coordinates, while most pixel points displayed are required to be interpolated using neighboring points on the polar coordinate. Conventionally, the interpolation algorithm applies a method of interpolating between neighboring points, which asks for a relatively small calculated amount and can be carried out much better for imaging in B-mode. An article by M. H. Lee et al., entitled "Analysis of a Scan Conversion Algorithm for a Real-Time Sector Scanner," published in IEEE Transactions on Medical Imaging, Vol. MI-5, No. 2 in June 1986 describes the noise resulting from the method using a DSC in B-mode and provides a solution. For example, as shown in FIG. 2, the algorithm via interpolation between neighboring points relates to estimation by interpolation using the ultrasonic wave information contained in the pixel points positioned on the polar coordinate in neighboring depth of two neighboring scan lines when the ultrasonic wave information in the corresponding points is calculated after the coordinates of the pixel points on the Cartesian coordinates are converted.

U.S. Pat. No. 5,429,137 by Robert N. Phelps et al., entitled "Acoustic scan conversion method and apparatus for velocity flow," describes how to perfect images of the colored blood flow via the DSC interpolation method. Such a method performs DSC interpolation processing not on the estimated velocity of the blood flow, but on the result from the autocorrelation algorithm that presents the velocity of the blood flow. In this method, DSC interpolation processing is carried out separately in the real parts and imaginary parts representing phase information in the ultrasonic echo signals, and is simultaneously conducted on the amplitude resulting from the autocorrelation algorithm and that of ultrasonic echo signals. These parameters are used for calculating the velocity variance of the blood flow, which represents turbulence of the blood flow. The specific interpolation algorithm does not utilize the method of linear interpolation between the neighboring points but rather a 2×4 interpolation kernel, which employs two-point linear interpolation along the scanning beam and four-point tertiary curve interpolation in a scan angle direction.

In B-mode, if the DSC module interpolates gray-scale signals using the algorithm via interpolation between neighboring points, noise caused by interpolation has less influence on images, but if the algorithm via interpolation between neighboring points is used to interpolate colored blood flow signals, more noise will be produced. In processing of colored blood flow signals, the phase and the amplitude can often be calculated by the autocorrelation algorithm, in which the velocity of motion, ranging from $-\pi$ to $\pi$ can be calculated according to the phase. The traditional interpolation between neighboring points is for processing the information on the phase and the amplitude, which is calculated through ultrasonic echo. Nevertheless, according to the Nyquist sampling theory, limitations of ultrasonic pulse repetition frequency can result in phase aliasing, which may lead to a suddenly abnormal blood flow in an opposite direction in the images showing the velocity of the normal blood flow. The algorithm via interpolation between neighboring points cannot identify the blood flow in the opposite direction caused by aliasing. In images for the blood flow, a blood flow at very low velocity could be formed as an apparent boundary between the normal blood flow and the abnormal blood flow because of interpolation processing. The noise from this interpolation will impact the doctor's judgment on aliasing.

If DSC interpolation processing is performed on the result from the autocorrelation algorithm instead of directly on the estimated velocity of the blood flow, noise resulting from the DSC interpolation algorithm can be reduced. However, this method requires a relatively huge amount of calculations and more storage volume to ensure calculation accuracy. In the interested regions of the colored blood flow, the autocorrelation algorithm can calculate the real parts, the imaginary parts, and the amplitude corresponding to each sampling volume of each scan line, in which the real parts and the imaginary parts can be used to calculate the velocity vector of motions by erythrocytes in the blood or by tissues. As is necessary to perform DSC processing on the real parts, the imaginary parts and the amplitude are calculated by the autocorrelation algorithm and then the velocity of the motion by the object is estimated; the entire dynamic range of every component needs to be preserved during DSC calculation.

Accordingly, there is a need for a scan conversion method and a scan conversion device for color ultrasonic imaging that is able to overcome the problem mentioned above.

According to one embodiment, a scan conversion method for color ultrasonic imaging is provided. The method comprises a storage step for storing ultrasonic echo data, a coordinate conversion step for performing coordinate conversion between an imaging coordinate system and a scan coordinate system, and an interpolation step comprising a substep for interpolation between neighboring points, a substep for determining aliasing and a substep for correcting echo data, in which the substep for interpolation between neighboring points is designated to obtain echo data of interpolation points by interpolating ultrasonic echo data of neighboring points, and the substep for determining aliasing is designated to determine whether or not aliasing occurs in ultrasonic echo data of neighboring points. If aliasing occurs, the substep for correcting echo data is performed, followed by the substep for interpolation between neighboring points; otherwise, the substep for correcting echo data is bypassed and the substep for interpolation between neighboring points is directly performed.

In the substep for determining aliasing, if the detected directions of the velocity of neighboring points are opposite and the difference therebetween is larger than the predetermined value, an occurrence of aliasing is determined. In one embodiment, the predetermined value is $\pi$.

Further, the substep for correcting echo data corrects ultrasonic echo data of neighboring points such that two ultrasonic echo data for interpolation are located at the same region having continuous changes.

In one embodiment, the substep for interpolation between neighboring points further comprises remapping of echo data value after interpolation into the range of values from $-\pi$ to $\pi$. Alternatively, the substep for correcting echo data further comprises confinement of corrected ultrasonic echo data to be equal to the maximum value $\pi$ or the minimum value $-\pi$, such that echo data after interpolation is automapped to the range of values from $-\pi$ to $\pi$.

In one configuration, the imaging coordinate system is a Cartesian coordinate system on a CRT screen or LCD screen, and the scan coordinate system is a polar coordinate system.

A scan conversion device for color ultrasonic imaging may be provided. In one embodiment, the device comprises a storage module for storing ultrasonic echo data, a coordinate conversion module for performing coordinate conversion between an imaging coordinate system and a scan coordinate system, and an interpolation module comprising a submodule for interpolation between neighboring points, a submodule for determining aliasing and a submodule for correcting echo data, in which the submodule for interpolation between neighboring points is designated to obtain echo data of interpolation points by interpolating ultrasonic echo data of neighboring points, and the submodule for determining aliasing is designated to determine whether or not aliasing occurs in ultrasonic echo data of neighboring points. If aliasing is found to be occurring, the submodule for correcting echo data corrects echo data of neighboring points and then interpolation occurs via the submodule for interpolating between neighboring points. If aliasing is not found to be occurring, the submodule for correcting echo data is bypassed and the submodule for interpolating between neighboring points is used to perform the interpolation.

In the submodule for determining aliasing, if the detected directions of the velocity of neighboring points are opposite and the difference therebetween is larger than the predetermined value, an occurrence of aliasing is determined.

In one configuration, the device further comprises a field programmable gate array (FPGA), in which the storage module 102, the coordinate conversion module 104, and the interpolation module 106 of FIG. 1 are all disposed.

Accordingly, an algorithm is introduced with "conditional" interpolation between neighboring points. A substep is provided for determining whether or not aliasing occurs in echo signals, such that if aliasing is determined, echo data can be corrected by the substep for correcting echo data, and corrected echo data is interpolated between the neighboring points, thus reducing noise resulting from interpolation. The algorithm can identify aliasing in the blood flow due to insufficient ultrasonic pulse repetition frequency, and then perform conditional interpolation between neighboring points in view of aliasing. Scan conversion based on an algorithm with conditional interpolation between neighboring points can be immediately applied to the colored blood flow signals, which not only reduces noise in the blood flow caused by interpolation, but also prevents DSC interpolation processing on the result from a large amount of autocorrelation, thereby consuming less storage volume and a lower amount of calculations.

The following examples of ultrasonic diagnosis are described in combination with the accompanying drawings to illustrate a scan conversion method and device for color ultrasonic imaging. It is to be noted that the disclosed method and device can be applied in various fields relating to ultrasonic imaging, such as the study of fluid kinematics and the detection of hydraulic pressure in pipelines, and should not be construed to be limited solely to the medical ultrasonic imaging field.

Figure 3:
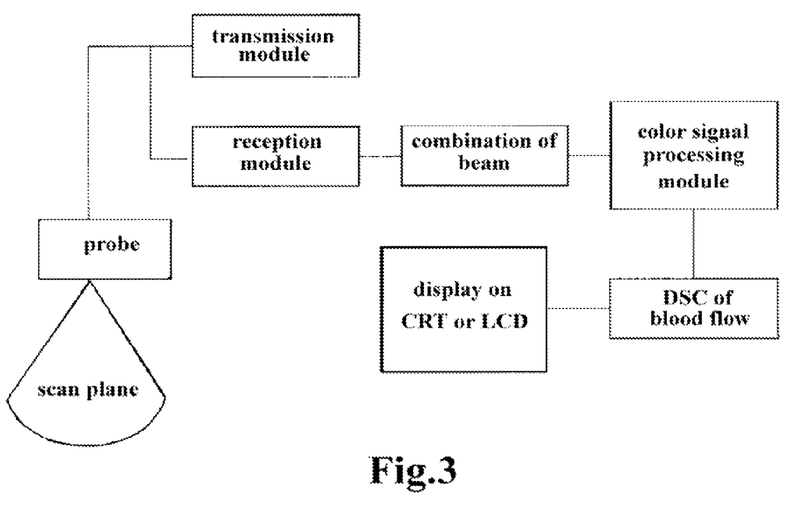
FIG. 3 is a schematic block diagram of a color Doppler system.

FIG. 3 is a schematic block diagram of a typical ultrasonic diagnostic system, which includes the blood flow DSC module of the present disclosure that converts blood flow signals into a format suitable for CRT or LCD display. Before describing a method involving colored DSC according to the present disclosure, a conventional DSC method is described for a better understanding of the improvement.

Figure 4:
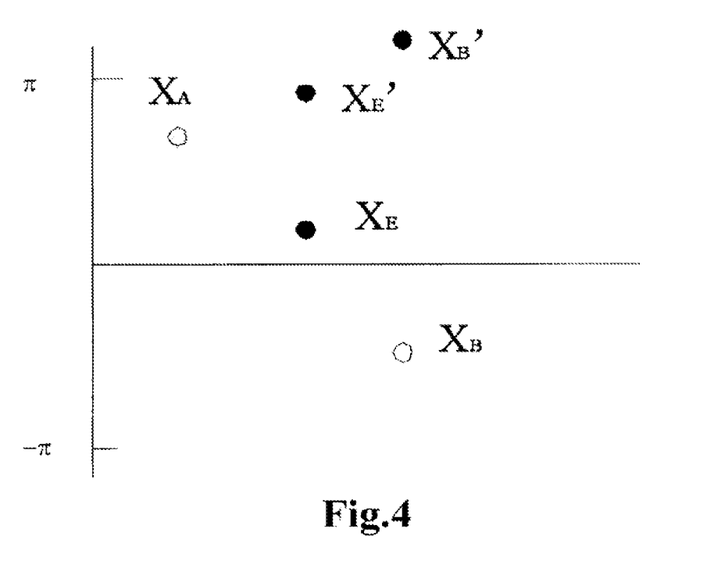
FIG. 4 is a graph showing interpolation between neighboring points with corrected blood flow values, wherein information $X_E$ at point E is obtained by interpolating the echo information $X_A$ and $X_B$ of point A and point B.

As shown in FIG. 4, it is supposed that two neighboring points A and B are sampled during DSC interpolation, in which the velocity of Point A detected is in a positive direction with the phase of the autocorrelation algorithm between zero and $\pi$, and the velocity of Point B detected to be in a negative direction due to aliasing with the phase of autocorrelation algorithm between $-\pi$ and zero. If the sampling ratio of the scan lines is sufficient, the velocity of Point E between Point A and Point B should be larger than that of $X_A$ in the positive direction (no aliasing) or less than $X_B$ (aliasing). When aliasing occurs in the velocity of the blood flow, $X_A$ and $X_B$, which are virtually not continuously changing, are supposed to be continuously changing according to conventional DSC interpolation; thereby the value $X_E$ at point E obtained by interpolation is between $X_A$ and $X_B$, i.e., less than $X_A$ and more than $X_B$. The value obtained by conventional DSC interpolation is larger than the actual value, and the difference may increase aliasing and therefore impact the doctor's judgment.

The scan conversion method and device of the present disclosure are described in detail as follows. As shown in FIG. 2, the improved algorithm with interpolation between neighboring points also relates to estimation by interpolation using ultrasonic wave information contained in the pixel points positioned on the polar coordinate in neighboring depth of two neighboring scan lines when the ultrasonic wave information in the corresponding points is calculated after the coordinates of the pixel points on a Cartesian coordinate system are converted. The embodied method is described below. First, it is supposed that the angle between two neighboring scan lines is normalized as 1 and the distance between two neighboring points along the direction of depth is normalized as 1. After conversion of the coordinate of a pixel G on a Cartesian coordinate system on a CRT or LCD screen, four corresponding neighboring points in echo data, indicated as A, B, C and D, can be identified, in which the scan depth of points A and B is the same, as is that of points C and D; points A and C are located at a common scan line n, and points B and D are located at a common scan line n+1. It might also mark the corresponding ultrasonic echo information corresponding to the four points $X_A$, $X_B$, $X_C$, $X_D$, respectively.

Second, it is supposed that the normalized angle between polar coordinates corresponding to point G and the scan line n is supposed to be $\theta_1$ (angle between the scan lines n and n+1 is defined as 1), and then the normalized angle between polar coordinates corresponding to point G and the scan line n+1 is $1-\theta_1$.

Third, it is supposed that the normalized distance in an axial direction between the polar coordinates corresponding to point G and point A in an axial direction is R (axial distance between points A and C is defined as 1), and then the normalized distance in an axial direction between polar coordinates corresponding to point G and point C in the axial direction is 1-R. Thus information $X_E$ in point E is first obtained by interpolation according to the ultrasonic wave information of points A and B. Thereafter, information $X_F$ in point F is obtained by interpolation according to the ultrasonic wave information of points C and D. Finally, information $X_G$ in point G is obtained by interpolation according to the ultrasonic wave information of points E and F.

The improved algorithm via interpolation between neighboring points also uses the normalized angle and distance as weight to process the interpolation algorithm. Before interpolation, however, the occurrence of aliasing in the blood flow should first be determined. If there is aliasing, correction of the blood flow value for interpolation is required.

Figure 5:
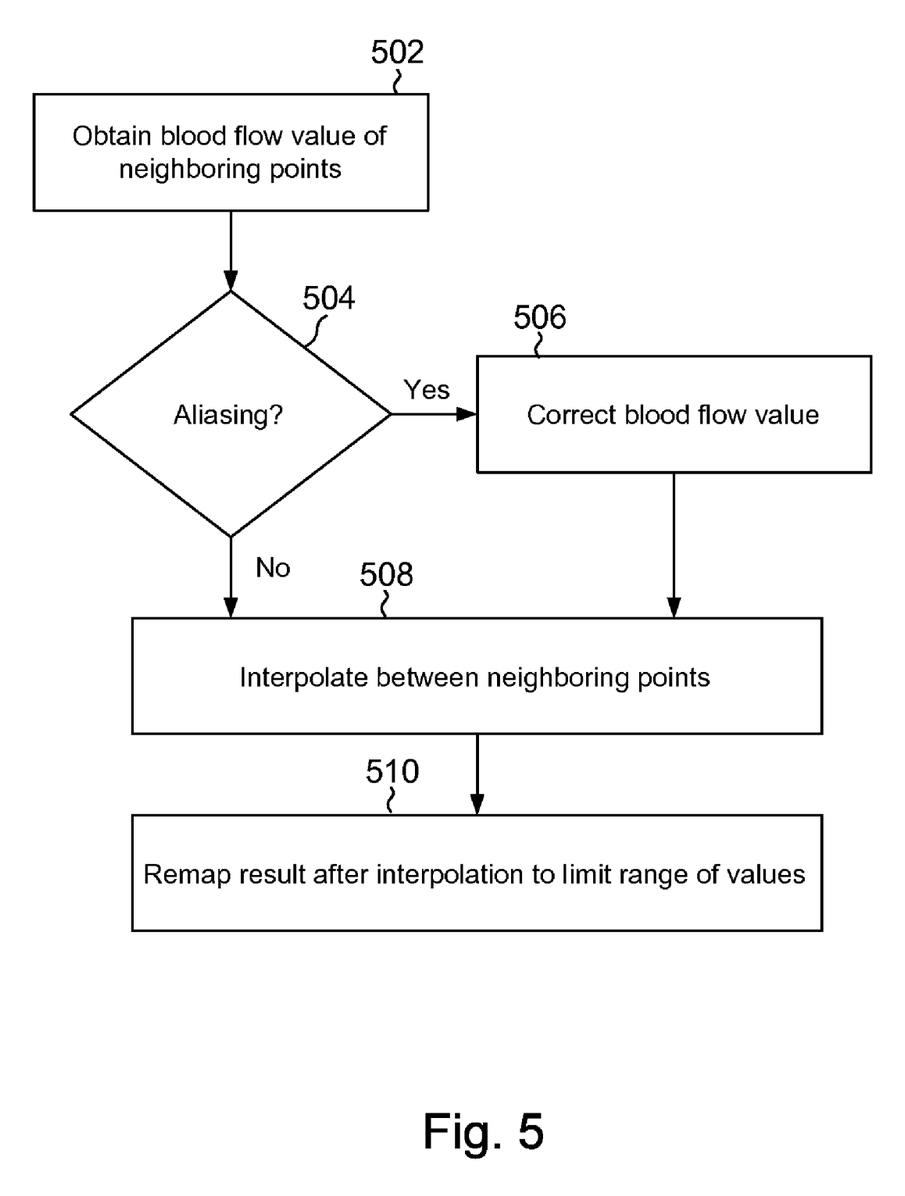
FIG. 5 is a flowchart of an algorithm for interpolating between neighboring points, which may be used in a scan conversion method for color ultrasonic imaging according to an embodiment.

As shown in FIG. 5, the blood flow value of neighboring points is obtained 502. If aliasing in the blood flow is determined 504, the blood flow value for interpolation is corrected 506; otherwise, there is no need for correction to the blood flow value. Correction of the blood flow value is aimed at positioning the two blood flow values for interpolation in the same region having continuous changes. The corrected blood flow values are interpolated 508 using the conventional method of interpolation between neighboring points. Finally, the result after interpolation is remapped 510 to the range of values from $-\pi$ to $+\pi$.

In one embodiment, if directions of two blood flow values are opposite and the absolution value of the difference therebetween is larger than the predetermined threshold, the occurrence of aliasing in the blood flow values may be determined. As shown in FIG. 4, $X_A$ is located between zero and $\pi$, and $X_B$ is located between $-\pi$ and zero. If $abs(X_A-X_B)$ is larger than Threshold, $X_A$ and $X_B$ need correcting to be $X'_A$ and $X'_B$, wherein abs represents the absolution algorithm and Threshold indicates a threshold that can be set according to actual condition, generally as $\pi$.

The object of correcting the blood flow value is to position the two blood flow values for interpolation in the same region having continuous changes. In one embodiment, the normalized angle $\theta_1$ defined by the distance between interpolation point E and point A is probably taken as a determination criterion (or the normalized distance in the axial direction is R). If $\theta_1$ (or R) is not more than 0.5 and $X_A$ is constant, $X_B$ is required to be corrected. If $\theta_1$ (or R) is more than 0.5 and $X_B$ is constant, $X_A$ is required to be corrected. As shown in FIG. 4, $\theta_1$ is supposed to be less than 0.5. The correction is described as follows:

$$X'_A = X_A$$

$$X'_B = X_B + 2\pi.$$

After correction, $X'_B$ is located between $\pi$ and $2\pi$, thereby obtaining the following equation using neighboring points interpolation:

$$X'_E = X'_A*(1-\theta_1) + X'_B*\theta_1 = X_A*(1-\theta_1) + (X_B+2\pi)*\theta_1.$$

Finally, the result after interpolation is remapped into the range of values from $-\pi$ to $+\pi$:

$$X_E = \begin{cases} X'_E & X'_E < \pi \\ X'_E - 2\pi & X'_E > \pi. \end{cases}$$

As shown in FIG. 4, after conditional interpolation processing, echo information $X_E$ at point E should be larger than the velocity of $X_A$ in the positive direction (no aliasing) or smaller than $A_B$ (aliasing), which is in accordance with the actual circumstance.

In another embodiment, the corrected echo information value can be limited to be equal to the maximum $\pi$ or the minimum $-\pi$, and then the result of final interpolation is located into the range of values from $-\pi$ to $+\pi$. Accordingly, the need for remapping the interpolation result to the range of values from $-\pi$ to $+\pi$ is eliminated. As such, calculation is simplified without influencing the final display of images. As an example, consider echo information $X_E$ at point E obtained by interpolation of echo information $X_A$ and $X_B$ at points A and B. Echo information $X_F$ at point F is obtained by interpolation of echo information $X_C$ and $X_D$ at points C and D. Likewise, echo information $X_G$ at point G is obtained by interpolation of echo information $X_E$ and $X_F$ at points E and F.

The occurrence of aliasing is determined first, and then $X_A$ and $X_B$ are corrected to be $X'_A$ and $X'_B$. The correction equation is described as follows:

If abs $|X_A - X_B|$ > Threshold and sign($X_A$) ≠ sign($X_B$)

$$X'_A = \begin{cases} X_A & \text{if } \theta_1 \leq 0.5 \\ \pi & \text{if } \theta_1 > 0.5 \text{ and } X_A < 0 \\ -\pi & \text{if } \theta > 0.5 \text{ and } X_A > 0 \end{cases}$$

$$X'_B = \begin{cases} X_B & \text{if } \theta_1 > 0.5 \\ \pi & \text{if } \theta_1 \leq 0.5 \text{ and } X_B < 0 \\ -\pi & \text{if } \theta \leq 0.5 \text{ and } X_B > 0. \end{cases}$$

Otherwise $X'_A = X_A$ $X'_B = X_B$.

$X_E$ is then obtained by interpolation using the method of interpolation between neighboring points:

$$X_E = X'_A*(1-\theta_1) + X'_B*\theta_1.$$

Because corrected echo information has been limited in the range from $-\pi$ to $+\pi$ during correction of echo information, the result $X_E$ finally acquired by the interpolation algorithm also falls in the range $-\pi$ to $+\pi$. Accordingly, the need for remapping $X_E$ into the range from $-\pi$ to $+\pi$ is eliminated. Thus the algorithm can be simplified with little influence on the final result.

Figure 6:
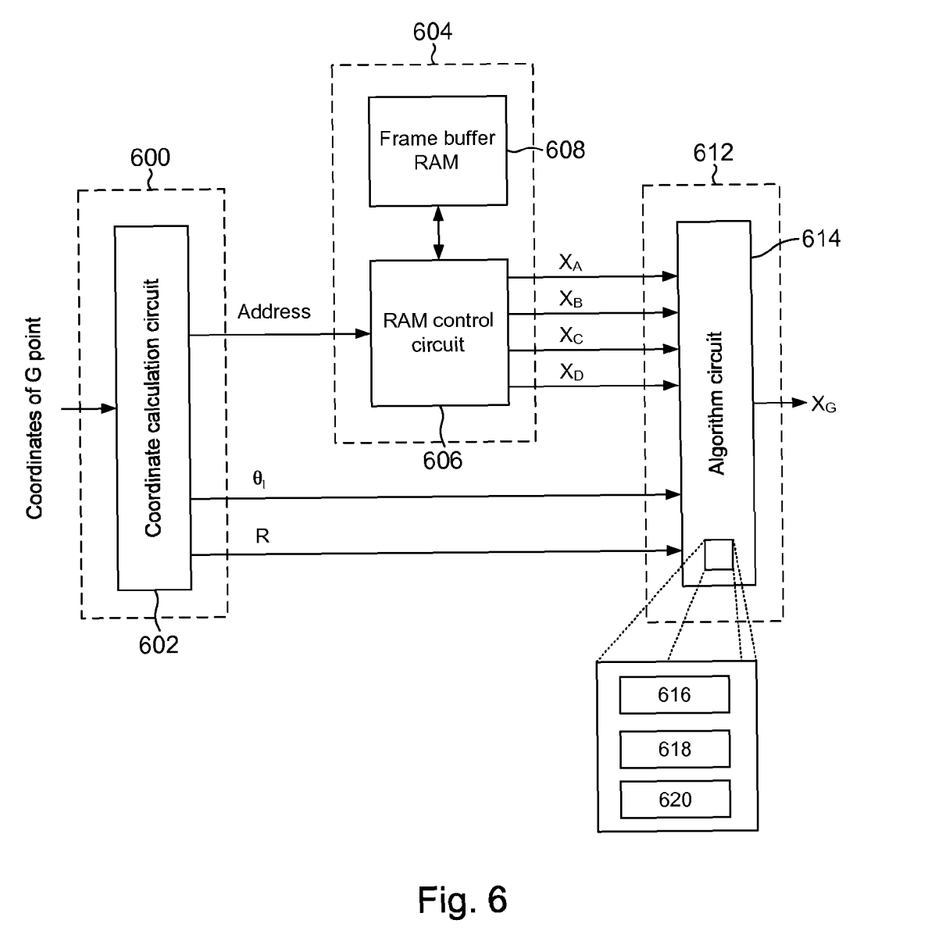
FIG. 6 is a block diagram of a field programmable gate array (FPGA) for implementing a scan conversion method for color ultrasonic imaging.

A device using the scan conversion method described above can be implemented using an FPGA, with details as shown in FIG. 6. A coordinate conversion module 600 may comprise coordinate calculation circuits 602 for obtaining Cartesian coordinates at point G on a CRT or LCD screen and converting Cartesian coordinates of point G into polar coordinates corresponding to the probe scan plane via the coordinate conversion circuits 602. In one embodiment, the module 600 divides the polar coordinates into integer addresses in relation to the receiving scan line and decimal values $\theta_1$ and R, as shown in FIG. 2. Four addresses can be gained for interpolation between neighboring points according to the integer addresses of polar coordinates on the scan line.

A storage module comprises 604 may comprise RAM (random access memory) control circuits 606 and frame buffer RAM 608, for storing ultrasonic echo data and reading corresponding colored blood flow values $X_A$, $X_B$, $X_C$ and $X_D$ from the frame buffer RAM in the storage module according to the four addresses.

An interpolation algorithm module 612 may be implemented using an algorithm circuit 614, which may have defined therein a submodule 616 for determining aliasing, a submodule 618 for correcting echo data and a submodule 620 for interpolating between neighboring points to calculate colored blood flow value $X_G$ at point G using the method of conditional interpolation between neighboring points described above according to colored blood flow values $X_A$, $X_B$, $X_C$ and $X_D$ and decimal values $\theta_1$ and R of polar coordinates.

The disclosed algorithm is an improvement on the algorithm via interpolation between neighboring points on the basis of processing gray-scale signals via DSC in B-mode. In C-mode, the improved algorithm via interpolation between neighboring points reduces noise resulting from aliasing as much as possible when processing blood flow signals. In displaying the velocity of the colored blood flow, the algorithm via interpolation between neighboring points with DSC is improved to become conditional. During the interpolation processing, the interpolation algorithm is used for comparing neighboring points for interpolation to determine whether or not aliasing occurs in the blood flow. When directions of the velocity at neighboring points are detected to be opposite and the difference therebetween is large, it is quite possible that aliasing occurs in the velocity detected. In this instance, the interpolation algorithm applies the processing mode of aliasing. As aliasing occurs, it is desirable to correct the velocity values of neighboring points in the interpolation algorithm for satisfying the requirement of aliasing. If there is no aliasing, a conventional interpolation algorithm is utilized. The present method and device directly perform DSC interpolation processing on the estimated velocity of the blood flow, but not on the result from the autocorrelation algorithm. Therefore the interpolation algorithm requires less storage and fewer calculations.

In one embodiment, the method of conditional interpolation between neighboring points is carried out using an FPGA. In C-mode, during processing of the velocity of the colored blood flow, velocity values displayed at every display point on a CRT or LCD screen are to be calculated via DSC interpolation processing. When conditional interpolation between neighboring points is performed, it is to be determined whether or not there is aliasing in the velocity values of neighboring points used for interpolation. If there is aliasing, the velocity values of neighboring points in the interpolation algorithm should be corrected. As only four-time multiplication or three-time addition are required for calculating every display point, the calculated amount is small and the entire DSC requires fewer resources for implementation. When operating the FPGA, only a system clock period is needed for calculating the velocity value of every display point with a flow-line design. Thus the velocity of the colored blood flow can be smoothly displayed on a CRT or LCD screen.

It has been verified through experiments that the scan conversion method according to the present invention can effectively reduce noise resulting from aliasing in the colored blood flow imaging.

Moreover, the disclosed conversion step may first perform pre-interpolation of the echo signal data according to predetermined pitch and interpolation density in the polar coordinate system, then perform coordinate conversion from the polar coordinate system to the Cartesian coordinate system, and finally directly display images into the Cartesian coordinate system according to converted Cartesian coordinate points and corresponding preinterpolation signal data. Put another way, the disclosed conversion step is not limited to conversion from the Cartesian coordinate system into the polar coordinate system.

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be understood by those having skill in the art that many changes may be made to the details of the above-described embodiments without departing from the underlying principles of the invention. The scope of the present invention should, therefore, be determined only by the following claims.

What is claimed is:

1. A scan conversion method for color ultrasonic imaging, comprising:
    a storage step for storing ultrasonic echo data;
    a coordinate conversion step for performing coordinate conversion between an imaging coordinate system and a scan coordinate system; and
    an interpolation step comprising a substep of interpolation between neighboring points, for obtaining ultrasonic echo data of an interpolation point by interpolating ultrasonic echo data of the neighboring points,
    wherein the interpolation step further comprises a substep for determining whether or not aliasing is occurring in the ultrasonic data of the neighboring points and a substep for correcting ultrasonic echo data, wherein if aliasing is found to be occurring, the substep for correcting ultrasonic echo data is performed followed by the substep of interpolation between neighboring points; otherwise, the substep for correcting ultrasonic echo data is bypassed and the substep of interpolation between neighboring points is directly performed.

2. The scan conversion method for color ultrasonic imaging according to claim 1, wherein aliasing is determined to be occurring if the detected directions of velocity of the neighboring points are opposite and the difference therebetween is larger than a predetermined value.

3. The scan conversion method for color ultrasonic imaging according to claim 2, wherein the predetermined value is $\pi$.

4. The scan conversion method for color ultrasonic imaging according to claim 3, wherein the substep for correcting ultrasonic echo data corrects the ultrasonic echo data of the neighboring points such that two ultrasonic echo data points for interpolation are located in the same region having continuous changes.

5. The scan conversion method for color ultrasonic imaging according to claim 4, wherein the substep for interpolation between neighboring points further comprises remapping of ultrasonic echo data values after interpolation into the range of values from $-\pi$ to $\pi$.

6. The scan conversion method for color ultrasonic imaging according to claim 4, wherein the substep for correcting ultrasonic echo data further comprises confinement of corrected ultrasonic echo data to be equal to the maximum value $\pi$ or the minimum value $-\pi$, such that ultrasonic echo data after interpolation is automapped into the range of values from $-\pi$ to $\pi$.

7. The scan conversion method for color ultrasonic imaging according to claim 6, wherein the imaging coordinate system is a Cartesian coordinate system of a cathode ray tube screen or liquid crystal display screen, and the scan coordinate system is a polar coordinate system.

8. The scan conversion method for color ultrasonic imaging according to claim 1, wherein the substep for correcting ultrasonic echo data corrects the ultrasonic echo data of the neighboring points such that two ultrasonic echo data points for interpolation are located in the same region having continuous changes.

9. The scan conversion method for color ultrasonic imaging according to claim 8, wherein the substep for interpolation between neighboring points further comprises remapping of ultrasonic echo data values after interpolation into the range of values from $-\pi$ to $\pi$.

10. The scan conversion method for color ultrasonic imaging according to claim 8, wherein the substep for correcting ultrasonic echo data further comprises confinement of corrected ultrasonic echo data to be equal to the maximum value $\pi$ or the minimum value $-\pi$, such that ultrasonic echo data after interpolation is automapped into the range of values from $-\pi$ to $\pi$.

11. The scan conversion method for color ultrasonic imaging according to claim 10, wherein the imaging coordinate system is a Cartesian coordinate system of a cathode ray tube screen or liquid crystal display screen, and the scan coordinate system is a polar coordinate system.

12. A scan conversion device for color ultrasonic imaging, comprising:
a storage module for storing ultrasonic echo data;
a coordinate conversion module for performing coordinate conversion between an imaging coordinate system and a scan coordinate system; and
an interpolation module comprising a submodule for interpolation between neighboring points, for obtaining ultrasonic echo data of an interpolation point by interpolating ultrasonic echo data of the neighboring points,
wherein the interpolation module further comprises a submodule for determining whether aliasing is occurring in the ultrasonic echo data of neighboring points and a submodule for correcting ultrasonic echo data if aliasing is determined to be occurring, such that if aliasing is determined to be occurring, the submodule for correcting ultrasonic echo data corrects the ultrasonic echo data of the neighboring points followed by interpolation between neighboring points by the interpolation module, and if aliasing is not determined to be occurring, the submodule for correcting ultrasonic echo data is bypassed and interpolation between neighboring points is directly performed by the interpolation module.

13. The scan conversion device for color ultrasonic imaging according to claim 12, wherein aliasing is determined to be occurring if the detected directions of velocity of neighboring points are opposite and the difference therebetween is larger than the predetermined value.

14. The scan conversion device for color ultrasonic imaging according to claim 13, wherein the predetermined value is $\pi$.

15. The scan conversion device for color ultrasonic imaging according to claim 12, wherein the submodule for correcting ultrasonic echo data corrects the ultrasonic echo data of the neighboring points such that two ultrasonic echo data points for interpolation are located in the same region having continuous changes.

16. The scan conversion method for color ultrasonic imaging according to claim 15, wherein the submodule for correcting ultrasonic echo data confines corrected ultrasonic echo data to be equal to the maximum value $\pi$ or the minimum value $-\pi$, such that ultrasonic echo data after interpolation is automapped into the range of values from $-\pi$ to $\pi$.

17. The scan conversion device for color ultrasonic imaging according to claim 12, wherein the submodule for interpolation between neighboring points remaps ultrasonic echo data values after interpolation into the range of values from $-\pi$ to $\pi$.

18. The scan conversion device for color ultrasonic imaging according to claim 12, further comprising a field programmable gate array, in which the storage module, the coordinate conversion module and the interpolation module are all disposed.

* * * * *